(12) United States Patent
Ferretti et al.

(10) Patent No.: US 10,220,038 B2
(45) Date of Patent: Mar. 5, 2019

(54) PHARMACEUTICAL COMBINATIONS

(71) Applicant: Novartis AG, Basel (CH)

(72) Inventors: Stephane Ferretti, Basel (CH); Sebastien Jeay, Basel (CH); Ensar Halilovic, Cambridge, MA (US); Fang Li, Cambridge, MA (US); Hui-Qin Wang, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/914,479

(22) Filed: Mar. 7, 2018

(65) Prior Publication Data

US 2018/0193346 A1 Jul. 12, 2018

Related U.S. Application Data

(63) Continuation of application No. 15/683,887, filed on Aug. 23, 2017, which is a continuation of application No. 15/423,855, filed on Feb. 3, 2017, which is a continuation of application No. 15/106,886, filed as application No. PCT/IB2014/067141 on Dec. 19, 2014.

(60) Provisional application No. 61/920,032, filed on Dec. 23, 2013, provisional application No. 62/078,571, filed on Nov. 12, 2014, provisional application No. 61/948,323, filed on Mar. 5, 2014.

(51) Int. Cl.
| | |
|---|---|
| *A61K 31/519* | (2006.01) |
| *A61K 31/4188* | (2006.01) |
| *A61K 31/505* | (2006.01) |
| *A61K 31/496* | (2006.01) |
| *A61K 31/506* | (2006.01) |

(52) U.S. Cl.
CPC ........ *A61K 31/519* (2013.01); *A61K 31/4188* (2013.01); *A61K 31/496* (2013.01); *A61K 31/505* (2013.01); *A61K 31/506* (2013.01)

(58) Field of Classification Search
CPC . A61K 31/495; A61K 31/4188; A61K 31/519
See application file for complete search history.

(56) References Cited

U.S. PATENT DOCUMENTS

| | | |
|---|---|---|
| 9,073,898 B2 | 7/2015 | Berghausen et al. |
| 9,416,136 B2 | 8/2016 | Besong et al. |

FOREIGN PATENT DOCUMENTS

| | | |
|---|---|---|
| WO | 2010/020675 | 2/2010 |
| WO | 2011/076786 A1 | 6/2011 |
| WO | 2012/066095 | 5/2012 |
| WO | 2013/111105 | 8/2013 |
| WO | 2014/172479 | 10/2014 |

*Primary Examiner* — San Ming R Hui
(74) *Attorney, Agent, or Firm* — Gregory Houghton

(57) ABSTRACT

The disclosure relates to a pharmaceutical combination of a mdm2/4 inhibitor, namely (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, and a cyclin dependent kinase 4/6 (CDK4/6) inhibitor 7-Cyclopentyl-2-(5-piperazin-1-yl-pyridin-2-ylamino)-7H-pyrrolo[2,3-d]pyrimidine-6-carboxylic acid dimethylamide. In addition, the disclosure relates to a pharmaceutical combination product. The disclosure also relates to corresponding pharmaceutical formulations, uses and treatment methods comprising said mdm2/4 inhibitor or a cyclin dependent kinase 4/6 (CDK4/6) inhibitor.

9 Claims, 3 Drawing Sheets

PHARMACEUTICAL COMBINATIONS

FIELD OF THE DISCLOSURE

The present disclosure relates to a pharmaceutical combination of an mdm2/4 inhibitor and a cyclin-dependent kinase 4/6 (CDK4/6) inhibitor. In addition, the disclosure relates to a pharmaceutical combination product. The disclosure also relates to corresponding pharmaceutical formulations, uses and treatment methods comprising mdm2/4 inhibitor or a cyclin dependent kinase 4/6 (CDK4/6) inhibitor.

BACKGROUND OF THE DISCLOSURE p53 mediates its function as a tumor suppressor through the transcriptional up-regulation of genes required for induction of cell cycle arrest or apoptosis (Vousden 2007, Nat Rev MCB; 8(4):275-83). It is estimated that about 50% of all tumors have lost, or carry an inactivating mutation in, p53 (Soussi 2001, Nature Rev Cancer; 1(3):233-240). In the remaining 50% of tumors, p53 is inactivated by various other means, including enhanced expression of its negative regulator, MDM2. MDM2 inhibitors can help restore the TP53 function.

The D-cyclin-CDK4/6-INK4a-pRb pathway is frequently disrupted in cancer to favor cell proliferation. Eighty percent of human neoplasms maintain functional pRb and instead increase CDK4/6 kinase activity to keep pRb inactivated via multiple aberrations. There are over 130,000 new cases of sarcoma worldwide each year, accounting for approximately 1% to 3% of all malignancies. Inhibitors of CDK4/6 are known that ameliorate effects of overactivated CDK4/6 kinase activity in tumors.

Liposarcoma (LPS) is a rare and heterogeneous disease that represents the most frequent soft tissue sarcoma in adults, accounting for approximately 12.8% of all sarcomas (Gadgeel 2009, Cancer; 115(12): 2744-2754). The annual incidence is estimated to be 2.5 per 1 million inhabitants in population-based studies (Kindblom 1975, Acta Pathol Microbiol Scand Suppl. (253):1-71). LPS is a malignant mesenchymal neoplasm that is composed of a varying proportion of mature adipocytic proliferation and a degree of cellular atypia. According to histology. LPS can be subdivided into five subtypes, i.e. well differentiated liposarcoma (WDLPS), dedifferentiated liposarcoma (DDLPS), myxoid liposarcoma, round cell liposarcoma, and pleomorphic liposarcoma, corresponding to three main biologic groups. Among these, the most common are the WDLPS (40-45% of all LPS) and DDLPS (5% of all LPS). WDLPS/DDLPS is considered as a biphasic disease, the dedifferentiated component being more aggressive and leading to metastasis. This component can either arise de novo or from the slowly growing well-differentiated component of the tumor.

In spite of numerous treatment options for patients with specific types of cancer, there remains a need for effective and safe combination therapies that can be administered for the effective long-term treatment of cancer.

SUMMARY OF THE DISCLOSURE

Both the MDM2 inhibitors and CDK4/6 inhibitors, as a monotherapy, demonstrate anti-proliferative and cytotoxic activities in in vitro and in vivo pre-clinical assays. Surprisingly it has been found that in combination. MDM2 inhibitors (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one (Compound A) or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one (Compound B) and a CDK4/6 inhibitor 7-Cyclopentyl-2-(5-piperazin-1-yl-pyridin-2-ylamino)-7H-pyrrolo[2,3-d]pyrimidine-6-carboxylic acid dimethylamide (Compound C) achieve greater antitumor activity than either drug alone. This effect was confirmed in a patient-derived well differentiated liposarcoma (WDLPS) in vivo model, where the combination of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one and 7-Cyclopentyl-2-(5-piperazin-1-yl-pyridin-2-ylamino)-7H-pyrrolo[2,3-d]pyrimidine-6-carboxylic acid dimethylamide induced tumor regression. Compound A, like Compound B is a potent and selective small molecule inhibitor of the p53:MDM2 interaction and the two share the exact same mechanism of action.

In WDLPS patient-derived in vivo model HSAX2655, which not only carried amplification of MDM2 gene but also CDK4 gene, combination of MDM2 and CDK4 inhibitors resulted in regressions. Daily (q24 h) treatment (p.o.) with Compound A at 30 mg/kg or Compound C at 75 mg/kg significantly slowed down the tumor growth (T/C of 6 and 18%, respectively) in tumor-bearing mice. However, the combination of the two drugs at these concentrations induced 36% tumor regression which was significantly better than with both monotherapies. Both single agent and combination treatments were well tolerated in mice.

Based on the optimistic findings the combination of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one with 7-Cyclopentyl-2-(5-piperazin-1-yl-pyridin-2-ylamino)-7H-pyrrolo[2,3-d]pyrimidine-6-carboxylic acid dimethylamide present a viable option for the treatment of proliferative disease such as cancer. Genetic status of cancer may further influence the utility of the combination. Best results can be expected in treating cancers with increased mdm2 and/or CDK4/6 activity. Wild-type status of p53 can further help.

Soft tissue sarcoma is a heterogeneous disease divided into five histologic subtypes, which include well differentiated liposarcoma (WDLPS) and dedifferentiated liposarcoma (DDLPS), the most common liposarcoma. Ninety percent of WDLS and DDLS display wild type status for p53 together with the amplification of the oncogenes MDM2 and CDK4. As a consequence, the combination of the compounds A or B together with the compound C offers a good therapeutic strategy for such cancers.

This notion can be expanded to a combination of other mdm2/4 inhibitors with other CDK4/6 inhibitors.

Therefore, more specifically, the present disclosure provides the following aspects, advantageous features and specific embodiments, respectively alone or in combination, as listed in the following items:
1. A pharmaceutical combination comprising
(i) (S)-1-(4-Chloro-phenyl)-7-isopropoxy-6-methoxy-2-(4-{methy-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, and (ii) 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof.

2. The pharmaceutical combination according to item 1, wherein the pharmaceutical combination comprises (i) (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, and (ii) 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof, separately or together.

3. The pharmaceutical combination according to item 1 or 2 for simultaneous or sequential use of the (i) (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, and (ii) 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof, as a medicine.

4. The pharmaceutical combination according to any one of items 1 to 3, further comprising at least one pharmaceutically acceptable carrier.

5. The pharmaceutical combination according to any one of items 1 to 4 in the form of a fixed combination.

6. The pharmaceutical combination according to any one of items 1 to 5 in the form of a pharmaceutical composition.

7. The pharmaceutical combination according to any one of items 1 to 6 in the form of a kit of parts for the combined administration, wherein the (i) (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, and (ii) 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof, are administered jointly or independently at the same time or separately within time intervals.

8. The pharmaceutical combination according to any one of items 1 to 7 for use as a medicine.

9. The pharmaceutical combination according to any one of items 1 to 7 for use in the treatment of cancer.

10. The pharmaceutical combination for use in the treatment of cancer according to item 9, wherein the cancer is ER positive breast cancers, melanoma, malignant rhabdoid tumor, neuroblastoma, lymphoma, mantle cell lymphoma or liposarcoma.

11. The pharmaceutical combination for use in the treatment of cancer according to item 9 or 10, wherein the cancer is liposarcoma.

12. The pharmaceutical combination for use in the treatment of cancer according to any one of items 9 to 11, wherein the cancer is well differentiated liposarcoma (WVDLPS) or dedifferentiated liposarcoma (DDLPS).

13. The pharmaceutical combination for use in the treatment of cancer according to any one of items 9 to 12, wherein the cancer comprises co-amplified MDM2 and/or CDK4.

14. The pharmaceutical combination for use in the treatment of cancer according to any one of items 9 to 13, wherein the cancer comprises functional p53 or is p53 wild-type.

15. The pharmaceutical combination according to any one of items 1 to 14 in the form of a combination product or a pharmaceutical composition.

16. The pharmaceutical combination according to any one of items 1 to 15 for the manufacture of a medicament or a pharmaceutical product for the treatment of cancer.

17. (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, for use as a medicament, wherein the (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof is to be administered simultaneously or sequentially with 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof.

18. (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, for use in the treatment of cancer, wherein the (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof is to be administered simultaneously or sequentially with 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof.

19. (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1- isopropyl-5,6-dihydro-1H-pyrrolo[3,4-d]imidazol-4-one, or a pharmaceutically acceptable salt thereof, for use in the treatment of cancer according to item 18, wherein the cancer is ER positive breast cancers, melanoma, malignant rhabdoid tumor, neuroblastoma, lymphoma, mantle cell lymphoma or liposarcoma.

20. (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or
(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, for use in the treatment of cancer according to item 18 or 19, wherein the cancer is liposarcoma.

21. (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or
(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, for use in the treatment of cancer according to any one of items 18 to 20, wherein the cancer is well differentiated liposarcoma (WDLPS) or dedifferentiated liposarcoma (DDLPS).

22. (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or
(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, for use in the treatment of cancer according to any one of items 18 to 21, wherein the cancer comprises co-amplified MDM2 and/or CDK4.

23. (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or
(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, for use in the treatment of cancer according to any one of items 18 to 22, wherein the cancer comprises functional p53 or is p53 wild-type.

24. A method for treating cancer in a patient comprising administering a therapeutically effective amount of (i) (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or
(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, and
(ii) 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof.

25. The method for treating cancer according to item 24, wherein (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or
(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, and
7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof, are administered to the patient simultaneously or sequentially.

26. The method for treating cancer according to item 24 or 25, wherein the cancer is as defined in any of the items 19 to 23.

27. The pharmaceutical combination according to any one of items 1 to 16, wherein the pharmaceutical combination consists of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or
(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, and
(ii) 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof.

28. Items according to any one of items 1 to 27, wherein the triple combination of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one
and 7-Cyclopentyl-2-(5-piperazin-1-yl-pyridin-2-ylamino)-7H-pyrrolo[2,3-d]pyrimidine-6-carboxylic acid dimethylamide with LDK378 is excluded.

29. Items according to any one of items 1 to 27, wherein the triple combination of 50 mg/kg qd po of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one
and 7-Cyclopentyl-2-(5-piperazin-1-yl-pyridin-2-ylamino)-7H-pyrrolo[2,3-d]pyrimidine-6-carboxylic acid dimethylamide with 50 mg/kg gd po of LDK378 is excluded.

30. Items according to any one of items 1 to 29, wherein the combination partners are (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or a pharmaceutically acceptable salt thereof, and 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof.

31. Items according to any one of items 1 to 29, wherein the combination partners are (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one or a pharmaceutically acceptable salt thereof, and 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof.

32. The pharmaceutical combination according to any one of items 1 to 16, or 27 to 29, (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, for use as a medicament according to any one of items 17, 28 or 29, (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, for use in the treatment of cancer according to any one of items 18 to 23, 28 or 29, the method for treating cancer according to any one of claims 24 to 26, 28 or 29, consisting of
(i) (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, or a pharmaceutically acceptable salt thereof, and
(ii) 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof.
33. The pharmaceutical combination according to any one of items 1 to 16, or 27 to 29,
(S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, for use as a medicament according to any one of items 17, 28 or 29. (S)-1-(4-Chloro-phenyl)-7-isopropoxy-8-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or
(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, for use in the treatment of cancer according to any one of items 18 to 23, 28 or 29, the method for treating cancer according to any one of claims 24 to 26, 28 or 29, consisting of
(i) (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, and
(ii) 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof.
34. The pharmaceutical combination according to any one of items 1 to 7 for use in the treatment of cancer according to any one of items 9 to 14, where (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one or (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, are to be administered every three weeks or every four weeks.
35. The pharmaceutical combination according to any one of items 1 to 7 for use in the treatment of cancer according to item 34, wherein (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one is used.

DETAILED DESCRIPTION OF THE DISCLOSURE

Figure 1:
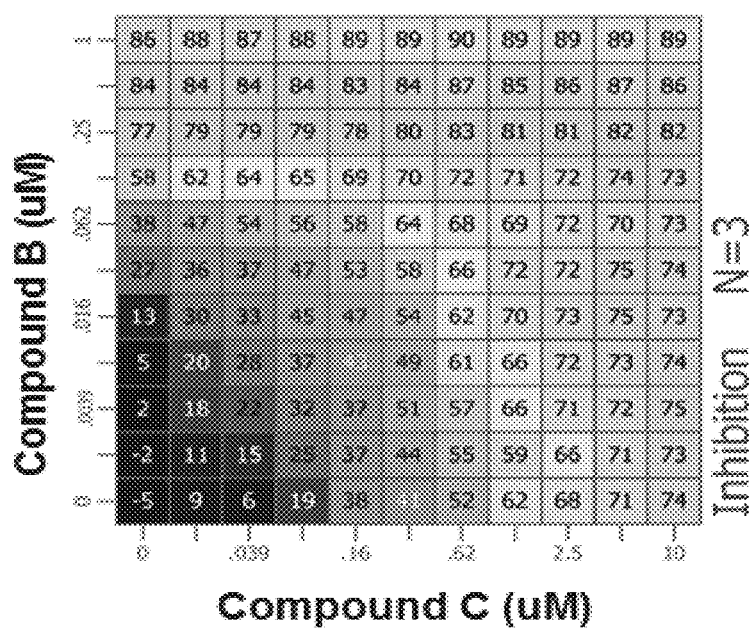
FIG. 1 Graphic representation of the in vitro effect on proliferation of the combination of compounds B and C in liposarcoma cell line LP6.
Figure 1:
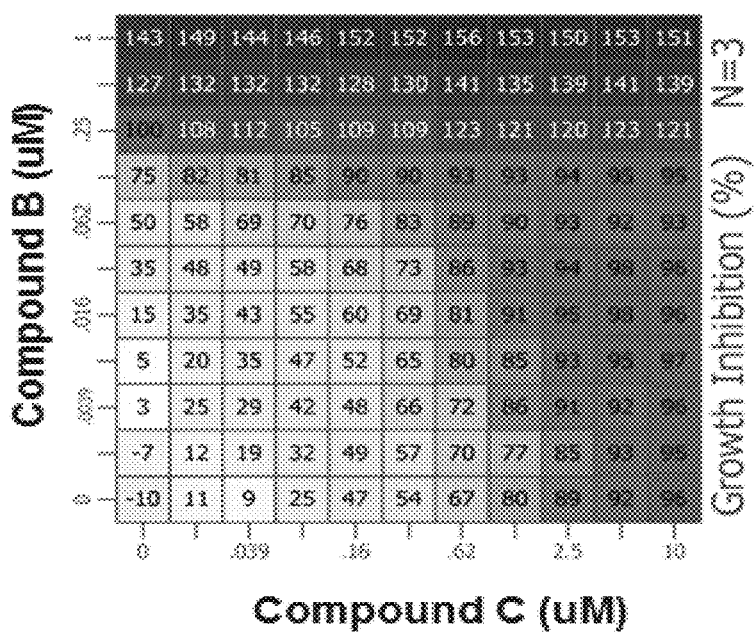

The present disclosure provides a pharmaceutical combination comprising (i) a Mdm2/4 inhibitor and (ii) a CDM4/6 inhibitor, wherein the mdm2/4 inhibitor is either (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, pharmaceutically acceptable salt thereof, or
(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, and the CDK4/6 inhibitor is
7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof.

It has been determined that the combination could be used to efficiently treat cancer.

The mdm2 inhibitor (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one (Compound A), can be prepared according to WO 2011/076786. The Compound A was disclosed in WO 2011/076786 as example 106. (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one (Compound A) is depicted in formula I

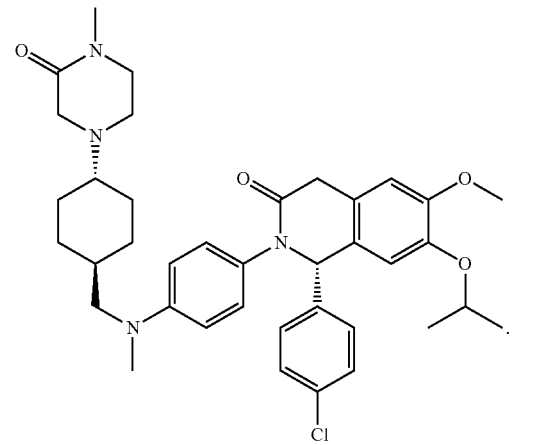

formula (I)

(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one (Compound B) inhibits the interaction between MDM2 and p53 while it also inhibits the interaction between MDM4 and p53. Its preparation was described in WO2013/111105. The compound can be presented with formula II formula (II)
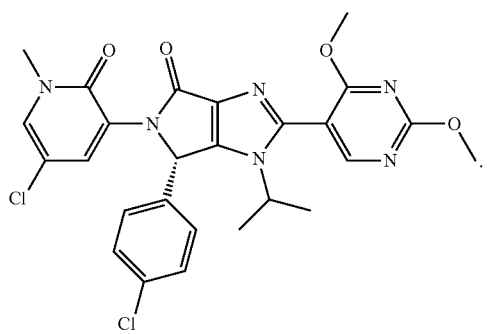
The mdm2/4 inhibitor that can be combined with the compound C, or used for the treatment of cancer as described herein, can also be for example a compound selected from the group consisting of:
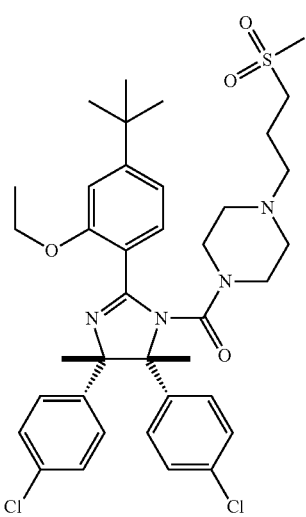
RG7112
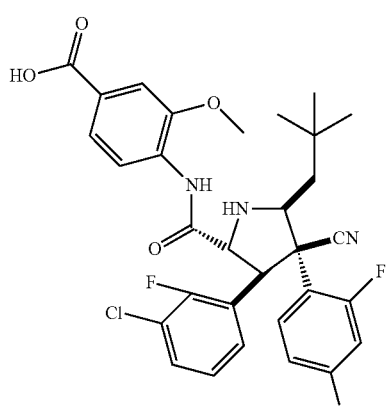
RG7388
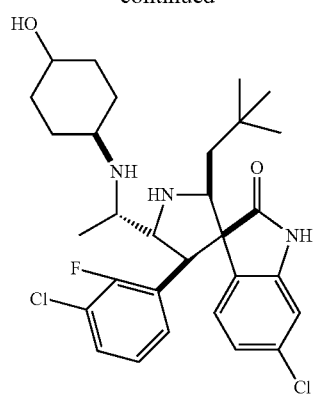
SAR299155
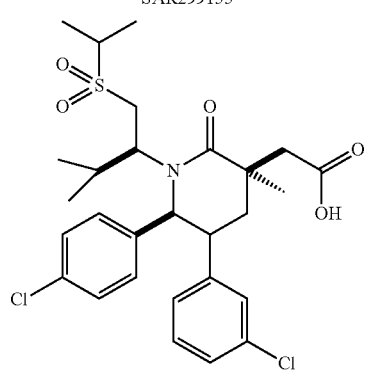
AMG 232
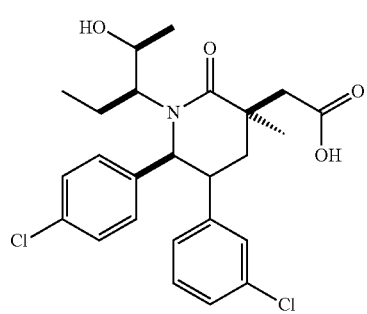
AM-8553
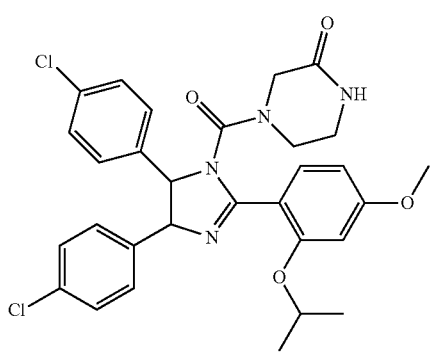
Nutlin-3

-continued

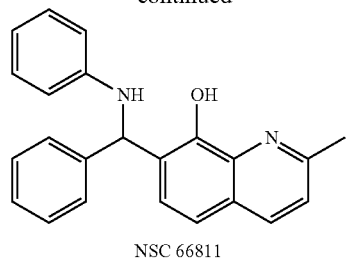

NSC 66811

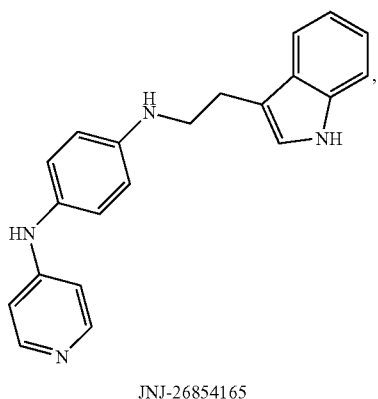

JNJ-26854165

Caylin-1, Caylin-2, HLI373, and SC204072.

7-Cyclopentyl-2-(5-piperazin-1-yl-pyridin-2-ylamino)-7H-pyrrolo[2,3-d]pyrimidine-6-carboxylic acid dimethylamide (Compound C) is the CDK4/6 inhibitor of formula III

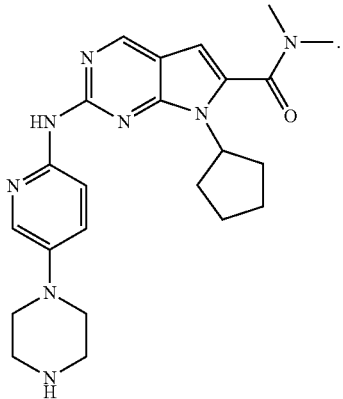

formula (III)

that was described in WO 2010/020675.

The compounds of the present combination can be used as a pharmaceutically acceptable salt, hydrate or a solvate. As used herein, "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from nontoxic inorganic or organic acids. Suitable organic acids are, e.g., carboxylic acids or sulfonic acids, such as acetic acid, succinic acid, fumaric acid or methansulfonic acid. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety. For example, the salt is a sulphate salt, or bisulphate salt. In another embodiment, the salt is a succinic salt. It is further contemplated that hydrates or solvates of the three compounds A, B and C can also be used.

The compounds of the pharmaceutical combination can be together or separate. This means that the "Pharmaceutical combination" of Compounds (A or B) and C refers to use, application or formulations of the separate partners with or without instructions for combined use or to combination products. The combination partners may thus administered entirely separately or be entirely separate pharmaceutical dosage forms. The combination partners may be pharmaceutical compositions that are also sold independently of each other and where just instructions for their combined use are provided in the package equipment, e.g. leaflet or the like, or in other information e.g. provided to physicians and medical staff (e.g. oral communications, communications in writing or the like), for simultaneous or sequential use for being jointly active. It can thus refer to either a fixed combination in one dosage unit form, or a kit of parts for the combined administration where Compound A or Compound may be administered independently of Compound C at the same time or separately within time intervals, especially where these time intervals allow that the combination partners show a coope-rative (=joint) effect. In one embodiment the effect of the combination is synergistic.

The terms "co-administration" or "combined administration" or "combined use" or the like as utilized herein are meant to encompass administration of the selected combination partner to a single subject in need thereof (e.g. a patient), and are intended to include treatment regimens in which the agents are not necessarily administered by the same route of administration and/or at the same time.

In one embodiment the pharmaceutical combination is a fixed combination. The term "fixed combination" means that the active ingredients, e.g. Compound A or Compound B are both administered to a patient simultaneously with Compound C in the form of a single entity or dosage. In other terms: the active ingredients are present in one dosage form, e.g. In one tablet or in one capsule.

The term "non-fixed combination" means that the active ingredients are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients. The term "non-fixed combination" thus defines especially administration, use, composition or formulation in the sense that the combination partners, for example (i) the mdm2 inhibitor (Compound A or B) and (ii) the CDK4/6 inhibitor (Compound C) as defined herein can be dosed independently of each other or by use of different fixed combinations with distinguished amounts of the combination partners, i.e. simultaneously or at different time points, where the combination partners may also be used as entirely separate pharmaceutical dosage forms or pharmaceutical formulations that are also sold independently of each other and just instructions of the possibility of their combined use is or are provided in the package equipment, e.g. leaflet or the like, or in other information e.g. provided to physicians and medical staff. The independent formulations or the parts of the formulation, product, or composition, can then, e.g. be administered simultaneously or chronologically staggered, that is at different time points and with equal or different time intervals for any part of the kit of parts. Particularly, the time intervals are chosen such that the effect on the treated disease in the combined use of the parts is larger than the effect which would be obtained by use of only any one of the combination partners (i) and (ii), thus being jointly active. Whether this is the case can, inter alia, be determined by following the blood levels, showing that both compounds are present in the blood of the human to be treated at least during certain time intervals. The ratio of the total amounts of the combination partner (i) to the combination partner (ii) to be administered in the combined preparation can be varied, e.g. in order to cope with the cancer to be treated or needs of a patient sub-population to be treated or the needs of the single patient which different needs can be due to age, sex, body weight, etc. of the patients.

In the combination therapies of the disclosure, the compounds useful according to the disclosure may be thus manufactured and/or formulated by the same or different manufacturers. Moreover, the combination partners may be brought together into a combination therapy: (i) prior to release of the combination product to physicians (e.g. in the case of a kit comprising the compound of the disclosure and the other therapeutic agent); (ii) by the physician themselves (or under the guidance of a physician) shortly before administration; (ill) in the patient themselves, e.g. during sequential administration of the compound of the disclosure and the other therapeutic agent.

In one embodiment, data carrier comprising information about using (i) the mdm2 inhibitor and (ii) the CDK4/6 inhibitor, simultaneously or sequentially, is provided. The data carrier, for example in a form of a product information leaflet or a label, packaging, brochure or web page instruction can be used to instruct to administer (i) Compound A or Compound B, or a pharmaceutically acceptable salt thereof, and (ii) Compound C, or a pharmaceutically acceptable salt thereof, simultaneously or sequentially for the treatment of cancer. The data carrier is particularly useful in the event the two partners of the combination are not formulated together, and supplied or sold separately. Each of the partners can be supplied with the data carrier, or even have the data carrier detached or provided separately, that informs or instructs about the possibility to use the combination partner in a pharmaceutical combination of the present disclosure. The data carrier can be used for the same purpose also in fixed combinations or situations, where both partners are supplied or sold together.

The present disclosure further provides a commercial package comprising as therapeutic agents a combination comprising: (a) Compound A or Compound B. and (b) compound C, and optionally at least one pharmaceutically acceptable carrier for use in the preparation of a pharmaceutical composition, together with instructions for simultaneous, separate or sequential administration thereof for use in the treatment of cancer.

The pharmaceutical combinations can further comprise at least one pharmaceutically acceptable carrier. As used herein, the term "carrier" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Generally, the term "pharmaceutical composition" is defined herein to refer to a mixture or solution containing at least one therapeutic agent to be administered to a subject, e.g., a mammal or human. The present pharmaceutical combinations can be formulated in a suitable pharmaceutical composition for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units. The pharmaceutical composition may contain, from about 0.1% to about 99.9%, preferably from about 1% to about 60%, of the therapeutic agent(s). One of ordinary skill in the art may select one or more of the aforementioned carriers with respect to the particular desired properties of the dosage form by routine experimentation and without any undue burden. The amount of each carriers used may vary within ranges conventional in the art. The following references disclose techniques and excipients used to formulate oral dosage forms. See *The Handbook of Pharmaceutical Excipients*, 4$^{th}$ edition, Rowe et al., Eds., American Pharmaceuticals Association (2003); and *Remington: the Science and Practice of Pharmacy*, 20$^{th}$ edition, Gennaro, Ed., Lippincott Williams & Wilkins (2003). These optional additional conventional carriers may be incorporated into the oral dosage form either by incorporating the one or more conventional carriers into the initial mixture before or during granulation or by combining the one or more conventional carriers with granules comprising the combination of agents or individual agents of the combination of agents in the oral dosage form. In the latter embodiment, the combined mixture may be further blended, e.g., through a V-blender, and subsequently compressed or molded into a tablet, for example a monolithic tablet, encapsulated by a capsule, or filled into a sachet. Clearly, the pharmaceutical combinations of the present disclosure can be used to manufacture a medicine.

The present disclosure relates to such pharmaceutical combinations that are particularly useful as a medicine. Specifically, the combinations can be applied in the treatment or prevention of a proliferative disease such as cancer. Cancer can be for example ER positive breast cancer, melanoma, malignant rhabdoid tumor, neuroblastoma, lymphoma, mantle cell lymphoma or liposarcoma. In a preferred embodiment the cancer is liposarcoma. Particularly the cancer is well differentiated liposarcoma (WDLPS) or dedifferentiated liposarcoma (DDLPS). The combination is expected to achieve superior effects in cancers with co-amplified MDM2 and/or CDK4. In addition, functional p53 or p53 wild-type could help increase the efficacy of the combination. The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present disclosure, the term "treat" also denotes to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject, e.g., a mammal or human. The term "prevent", "preventing" or "prevention" as used herein comprises the prevention of at least one symptom associated with or caused by the state, disease or disorder being prevented.

The nature of cancer is multifactorial. Under certain circumstances, drugs with different mechanisms of action may be combined. However, just considering any combination of therapeutic agents having different mode of action does not necessarily lead to combinations with advantageous effects. The administration of a pharmaceutical combination of the disclosure may result not only in a beneficial effect, e.g. a synergistic therapeutic effect, e.g. with regard to alleviating, delaying progression of or inhibiting the symptoms, but also in further surprising beneficial effects, e.g. fewer side-effects, an improved quality of life or a decreased morbidity, compared with a monotherapy applying only one of the pharmaceutically therapeutic agents used in the combination of the disclosure. A further benefit is that lower doses of the therapeutic agents of the combination of the disclosure can be used, for example, that the dosages need not only often be smaller, but are also applied less frequently, or can be used in order to diminish the incidence of side-effects observed with one of the combination partners alone. This is in accordance with the desires and requirements of the patients to be treated. It can be shown by established test models that the combination of the disclosure results in the beneficial effects described herein before. The person skilled in the art is fully enabled to select a relevant test model to prove such beneficial effects. The pharmacological activity of a combination of the disclosure may, for example, be demonstrated in a clinical study or in a test procedure as essentially described hereinafter. The combination partners (i) and (ii) in any disclosure embodiment are preferably formulated or used to be jointly (prophylactically or especially therapeutically) active. This means in particular that there is at least one beneficial effect, e.g. a mutual enhancing of the effect of the combination partners (i) and (ii), in particular a synergism, e.g. a more than additive effect, additional advantageous effects (e.g. a further therapeutic effect not found for any of the single compounds), less side effects, a combined therapeutic effect in a non-effective dosage of one or both of the combination partners (i) and (ii), and very preferably a clear synergism of the combination partners (i) and (ii). For example, the compounds may be given separately or sequentially (in a chronically staggered manner, especially a sequence-specific manner) in such time intervals that they preferably, in the warm-blooded animal, especially human, to be treated, and still show a (preferably synergistic) interaction (joint therapeutic effect). A joint therapeutic effect can, inter alia, be determined by following the blood levels, showing that both compounds are present in the blood of the human to be treated at least during certain time intervals, but this is not to exclude the case where the compounds are jointly active although they are not present in blood simultaneously.

The term "pharmaceutically effective amount" or "clinically effective amount" of a combination of combination partners is an amount sufficient to provide an observable improvement over the baseline clinically observable signs and symptoms of the disorder treated with the combination.

The term "synergistic effect" as used herein refers to action of two therapeutic agents such as, for example, Compound A as the mdm2 inhibitor and Compound C as the CDK4/6 inhibitor, producing an effect, for example, slowing the symptomatic progression of a proliferative disease, particularly cancer, or symptoms thereof, which is greater than the simple addition of the effects of each drug administered by themselves. The same would apply to combination of Compound B and C. A synergistic effect can be calculated, for example, using suitable methods such as the Sigmold-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The present disclosure provides also a method of treating a subject having a proliferative disease, namely cancer, comprising the step of administering to said subject a pharmaceutical combination comprising (i) Compound A or Compound B and (ii) Compound C, and optionally at least one pharmaceutically acceptable carrier in a quantity, which is jointly therapeutically effective against cancer.

The term "subject" or "patient" as used herein includes animals, which are capable of suffering from or afflicted with a cancer or any disorder involving, directly or indirectly, a cancer. Examples of subjects include mammals, e.g., humans, dogs, cows, horses, pigs, sheep, goats, cats, mice, rabbits, rats and transgenic non-human animals. In the preferred embodiment, the subject is a human.

In one embodiment, a therapeutically effective amount of each of the combination partner of the combination of the disclosure may be administered simultaneously or sequentially and in any order, and the components may be administered separately or as a fixed combination. For example, the method of treating a proliferative disease according to the disclosure may comprise (i) administration of the first agent (a) in free or pharmaceutically acceptable salt form and (ii) administration of an agent (b) in free or pharmaceutically acceptable salt form, simultaneously or sequentially in any order, in jointly therapeutically effective amounts, preferably in synergistically effective amounts, e.g. in daily or intermittently dosages corresponding to the amounts described herein. The individual combination partners of the combination of the disclosure may be administered separately at different times during the course of therapy or concurrently in divided or single combination forms. Furthermore, the term "administering" also encompasses the use of a pro-drug of a combination partner that convert in vivo to the combination partner as such. The instant disclosure is therefore to be understood as embracing all such regimens of simultaneous or alternating treatment and the term "administering" is to be interpreted accordingly.

In general, the dosage of the compound A, B and C to be applied to a warm-blooded animal depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Compounds A and B can be generally administered in unit dosage of about 1-5000 mg of active ingredient(s) for a subject of about 50-70 kg, or about 1 mg-3 g or about 1-250 mg or about 1-150 mg or about 0.5-100 mg, or about 1-50 mg of active ingredient. The unit dosage may be administered once or repeatedly during the same day, or during the week. More specifically, daily dose of between 100 mg and 1500 mg, particularly between 300 mg and 1000 mg may be suitable for Compound A. For Compound B, doses between 10 mg and 1000 mg may be suitable. The daily dose between 50 mg and 1500 mg, particularly between 400 mg and 900 mg, preferably about 600 mg, is expected to be efficacious for Compound C. Daily doses of the compounds may require drug holidays. For example, the dosing regimen may include 3 weeks on the drug and 1 week off. The combination partners may not be administered according to the same dosing regimen. The compounds A or B can be used every 3 weeks or every 4 weeks. Particularly compound B can be used every 3 weeks. It can also be administered to a patient every 4 weeks. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

A combination product according to the disclosure can besides or in addition be administered especially for cancer therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemo-preventive therapy, for example in patients at risk.

The present disclosure further provides a commercial package comprising as therapeutic agents combination of the disclosure, together with instructions for simultaneous, separate or sequential administration thereof for use in the delay of progression or treatment of a proliferative disease in a subject in need thereof.

The following Examples illustrate the disclosure described above; they are not, however, intended to limit the scope of the disclosure in any way. The beneficial effects of the pharmaceutical combination of the present disclosure can also be determined by other test models known as such to the person skilled in the pertinent art.

Compound A: (S)-1-(4-Chloro-phenyl)-7-iso-propoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one Compound B: (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one Compound C: 7-Cyclopentyl-2-(5-piperazin-1-yl-pyridin-2-ylamino)-7H-pyrrolo[2,3-d]pyrimidine-6-carboxylic acid dimethylamide (possible form is [7-Cyclopentyl-N,N-dimethyl-2-{[5-(piperazin-1-yl)pyridin-2-yl]amino}-7H-pyrrolo[2,3-d] pyrimidine-6-carboxamide Succinate)

EXAMPLE 1: Well Differentiated Liposarcoma (WDLPS) Patient-Derived In Vivo Model HSAX2655

PDX tumors were induced by transplanting subcutaneously frozen pieces of tumors in the right flank of Harlan nude mice. After several weeks of growth, donor animals were sacrificed and tumors were taken out and cut in 3×3×3 mm$^3$ pieces. Each tumor piece was transplanted subcutaneously in the right flank of naive Harlan nude mice. Efficacy experiment could start 30 days post transplantation.

Compounds A and C were formulated fresh for each administration. The compounds were dissolved in 0.5% methylcellulose. For efficacy experiments, mice were randomized into groups of n=5 and treated for 14 days. Compound A was injected at 30 mg/kg and Compound C at 75, 150 and 250 mg/kg. Mice were treated daily (q24 h) p.o. at 10 ml/kg for both drugs. On the last day of experiment, mice from each treatment group were sacrificed 4 and 24 h post last treatment and tumors were snap-frozen.

Efficacy and tolerability were assessed by determining tumor volume and body weight, respectively. Tumor volume (TVol), determined from caliper measurements (using the formula l*w*h*π/6) were measured three times per week. Tumor response was quantified by the change in tumor volume (endpoint minus starting value in mm$^3$) as the T/C i.e.

$$\left(\frac{\Delta TVol_{drug}}{\Delta TVol_{vehicle}} \times 100\right).$$

In the case of tumor regression, the tumor response was quantified by the percentage of regression of the starting TVol, ie $$\left(\frac{\Delta TVol_{drug}}{TVol_{Day0}} \times 100\right).$$

The body-weight (BW) of the mice was measured three times per week allowing calculation at any particular timepoint relative to the day of initiation of treatment (day 0) of both the percentage change in BW (Δ % BW).

Differences between the means of TVol and BW were assessed on the endpoint ΔTvol or % ΔBW using a 1-way ANOVA with Dunnett or Tukey's tests post-hoc. Linear correlations were explored by determining Pearson correlation coefficient, with P<0.05 considered as significant.

A non-statistical analysis of the combination effects of therapy on the efficacy were calculated using a modification of the method described by Clark (1997) to obtain a Combination Index (CI). Thus, multiplication of the AUC-T/Cs for single agents A and B was compared to the AUC-T/C obtained for the actual combination A+B.

If $T/C_A * T/C_B > T/C_{AB}$ then a positive interaction could be assumed (CI<1.0)

If $T/C_A * T/C_B < T/C_{AB}$ then a negative interaction could be assumed (CI>1.0)

The same analysis could be done on the AUC of mRNA induction. However, in such case, we had to work with a ratio 1/CI as we are evaluating induction and not inhibition. By analogy to the in vitro analyses of combination interactions by Chou (1991), a more useful interpretation is that a CI of 0.7-1.3 indicates additivity, <0.7 indicates synergy and >1.3 indicates antagonism.

In WDLPS patient-derived in vivo model HSAX2655, which not only carries amplification of MDM2 gene but also CDK4 gene, combination of MDM2 and CDK4 inhibitors resulted in regressions. Daily (q24 h) treatment (p.o.) with Compound A at 30 mg/kg or Compound C at 75 mg/kg significantly slowed down the tumor growth (T/C of 6 and 18%, respectively) in tumor-bearing mice. However, the combination of the two drugs at these concentrations induced 36% tumor regression which was significantly better than with both monotherapies (Table 1). Both single agent and combination treatments were well tolerated in mice.

TABLE 1

Combination study with Compound A and Compound C in HSAX2655-tumor bearing mice

| Treatment | Efficacy/tolerability on day 37 post transplantation (day 14 post 1st treatment) | | | | |
|---|---|---|---|---|---|
| | Tumor | | | Host | |
| (p.o., q24h) | ΔTvol (mm³) | T/C (%) | Reg (%) | ΔBW(%) | Survival |
| Vehicle (10 ml/kg) | 377 ± 95 | — | — | 8.1 ± 2.1 | 5/5 |
| Compound A 30 mg/kg | 24 ± 12 [a] | 6 | — | 6.9 ± 2.0 | 5/5 |
| Compound C 75 mg/kg | 66 ± 18 [a] | 18 | — | 4.7 ± 2.3 | 5/5 |
| Combination | −43 ± 9 [abc] | — | −36 | 9.4 ± 1.6 | 5/5 |

P < 0.05 signifies significantly different to vehicle
[a] Compound A
[b] and Compound C
[c] (Tukey's one-way ANOVA).

EXAMPLE 2: Combination of Compound B and Compound C in Liposarcoma Cell Lines

Compounds B and C were dissolved in 100% DMSO (Sigma, Catalog number D2650) at concentrations of 10 mM and stored at −20° C. until use. Compounds were arrayed in 300 uL deep well 384-well plates (BrandTec, Catalog number 701355) at 8× the highest final concentration. Row and column dilutions were prepared separately using a Bravo liquid handler (Agilent Technologies). Dilutions were made at 1:2 giving a total of 10 dilutions for each compound. Once completed the row and column dilution plates were combined 1:1 giving a final stamping plate at 4× concentration.

The cell lines 449b, 778 and LP6 were cultured in RPMI1640 (ATCC, Catalog number 30-2110) supplemented with 10% FBS (HyClone, Catalog number SH30071.03) at 37° C. and 5% CO2. In all cases cells were thawed from frozen stocks, expanded through ≥1 passage using 1:6 dilutions. Cells were counted and assessed for viability using a ViCell counter (Beckman-Coulter). The identity of all the cell lines was confirmed by SNP profiling.

All cells were seeded at a concentration of $3.33\times10^4$ cells/mL in 30 uL RPMI1640 media using a BioTek Micro-Fill (BioTek). Four 384-well plates were prepared per cell line (Greiner bio-one, catalog number 781091). The next day, compound was added using Bravo liquid handler. One of the four plates (Day 0 plate), used to determine baseline cell viability did not receive compound and was immediately fixed and permeabilized (as described below). To other plates, compound was added and plates were incubated for 72 hrs. Following incubation period, 10 ul of the media was removed using the ELx405 Microplate Washer (BioTek/ Thermo Scientific). Cells were then fixed and permeabilized for 1 Hr (at room temperature) by adding 20 ul of a fixation-permeabilisation solution containing 10% Paraformaldehyde (SIGMA, P6148) and 0.3% Triton X-100 (Electron Microscopy Sciences, 22140) in PBS (SIGMA, P3744) using the WellMate plate dispenser (Matrix/Thermo Scientific, 201-10001) with a standard 8-channel cassette (Matrix/Thermo Scientific, 201-30001).

Fixed cells were washed three times by removing 20 ul from the wells with the microplate washer and by adding 60 ul PBS with the plate dispenser. Then, after removing 60 ul from the wells, the cells' DNA and actin were stained using Hoechst 33342 (Invitrogen, H3570, 10 mg/ml stock in water) and Alexa Fluor 488 phalloidin (A12379, Invitrogen, 6.6 uM stock in methanol), respectively. Both dyes were diluted 1:1000 in PBS and 40 ul were added to each well using the plate dispenser and incubated for 30 min (at room temperature). As a last step cells were washed three times with 60 ul PBS. Plates were sealed using a PlateLoc thermal microplate sealer (Agilent Technologies, G5402A) with aluminum pierceable seals (Agilent Technologies, 06644-001) at 178 degrees Celsius for 2.2 sec. Plates were imaged with the InCell Analyzer 2000 (GE Healthcare, 28-9534-63) using a 4× objective and the DAPI excitation/emission filters all nuclei per well were captured in a single image.

Images from the InCell Analyzer 2000 (GE Healthcare, 28-9534-63) were in TIFF format and had a size of 2048× 2048 pixels, capturing the whole well of a 384-well plate. An automated image analysis pipeline was established using custom-made scripts in the open-source, statistical programming language R, and functions of the BioConductor package EBImage. The goal was to quantify the number of viable nuclei (cells) per well as an approximation for cell viability. The pipeline was comprised of seven steps: (I.) smoothing of the image to reduce the number of intensity peaks, (II.) application of a threshold function to separate the foreground (signal) from the background (noise), (III.) identification of local maxima in the foreground that serve as seeds for the nuclei, (IV.) filtering of local maxima in close proximity. (V.) propagation of the nuclei from remaining local maxima, (VI.) and extraction of object features from the propagated nuclei (numbers of nuclei, size features and intensity features). As a last step (VII.), to exclude debris (e.g. fragmented nuclei) from counting, objects identified in DMSO- and Staurosporin-treated wells were used to obtain feature distributions for viable and fragmented nuclei, respectively. These were used to set cut-offs differentiating between viable and fragmented nuclei. The number of fragmented nuclei was subtracted from the total number of identified objects and the result was reported as final count for that well. Data comprised triplicate measurements for each treatment (compound) condition, and 189 replicates of DMSO-treated wells. The data was normalized to the median of the DMSO measurements and summarized by calculating the median of the triplicates. Data analysis was performed using Chalice Analyzer as described in (Lehar et al. 2009). Briefly, the average percent inhibition (relative to the DMSO treated control) for triplicate compound-treated wells at each concentration of compounds was determined and up-loaded into Chalice Analyzer Database. The following formula was used to calculate percent inhibition (1−(value/day 3 DMSO average))*100). HSA Excess score was calculated as described in (Lehar et al. 2009).

The growth inhibition was calculated next. First, the baseline (Day 0) viability was determined by quantifying the viability in 189 wells before treatment. The median of these measurements was subtracted from the measurements at the end of the experiment to differentiate between compound effects that lead to "killing" or "stasis"). Baseline-subtracted measurements were imported to Chalice to calculate growth inhibition. The following formula was used to calculate the growth inhibition: IF value<day 0 DMSO, ((value−day 0 DMSO)/day 0 DMSO)*100. IF value>day 0 DMSO, ((value−day 0 DMSO)/(day 3 DMSO−day 0 DMSO))*100. Growth inhibition result of 0=no growth inhibition, 100=stasis and 200=complete killing.

Both Compound B and Compound C as single agents strongly inhibited the growth of all three cell lines. Compound B IC50 values were 27.7 nM, 46.6 nM, and 86 nM in 449b, 778, and LP6 cells respectively. Compound C IC50 values were 130 nM, 59.3 nM, and 475 nM in 449b, 778, and LP6 were respectively.

Figure 2:
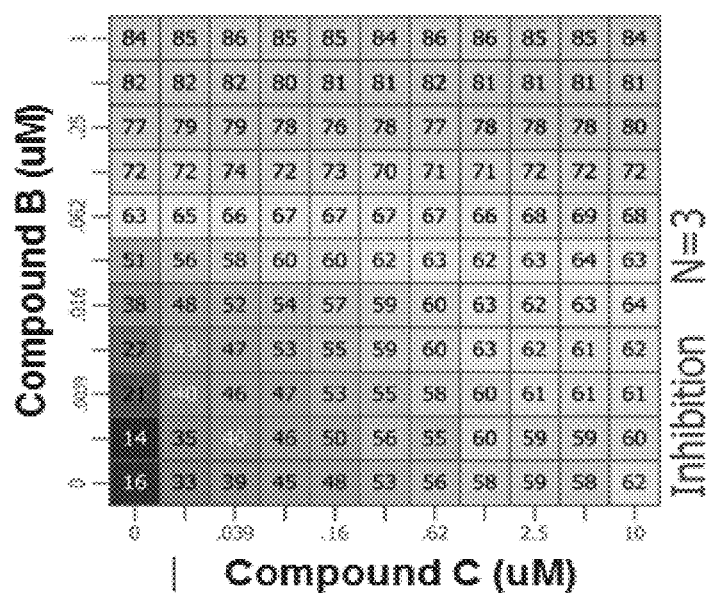
FIG. 2 Graphic representation of the in vitro effect on proliferation of the combination of compounds B and C in liposarcoma cell line 449b.
Figure 2:
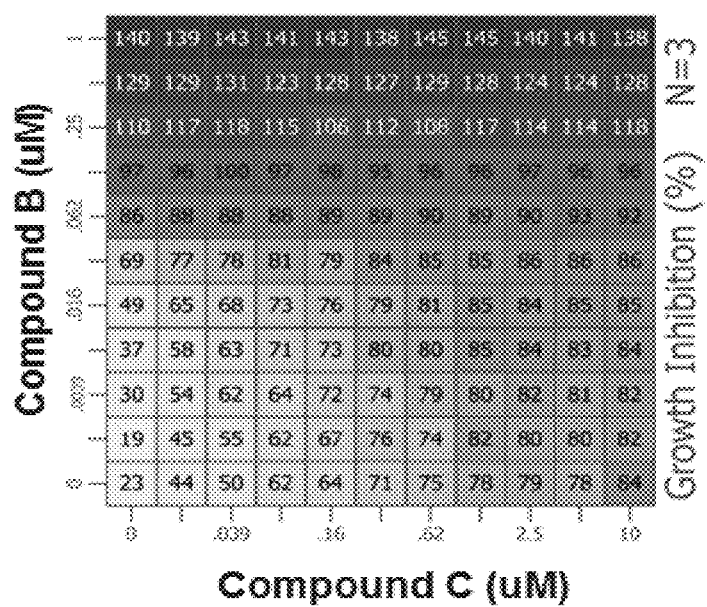
Figure 3:
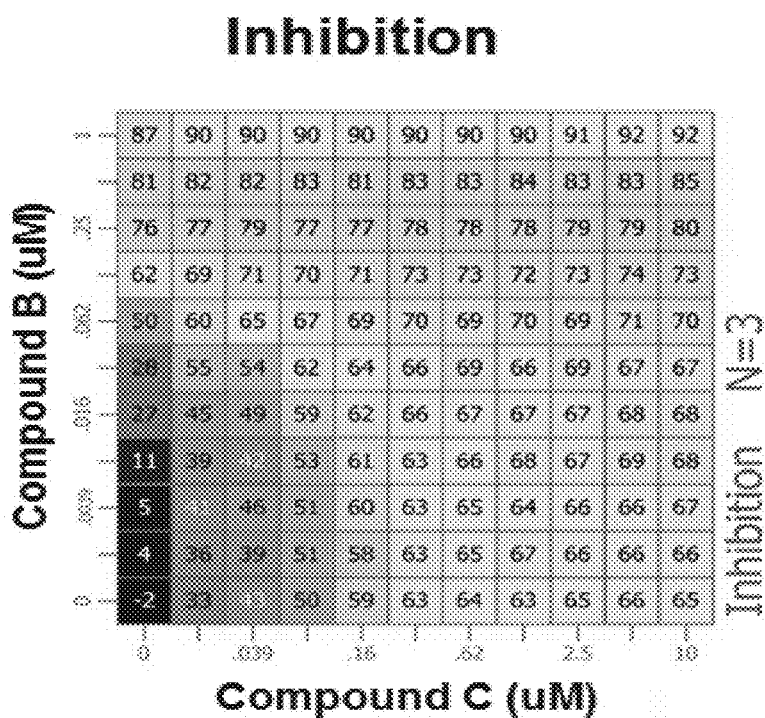
FIG. 3 Graphic representation of the in vitro effect on proliferation of the combination of compounds B and C in liposarcoma cell line T778.
Figure 3:
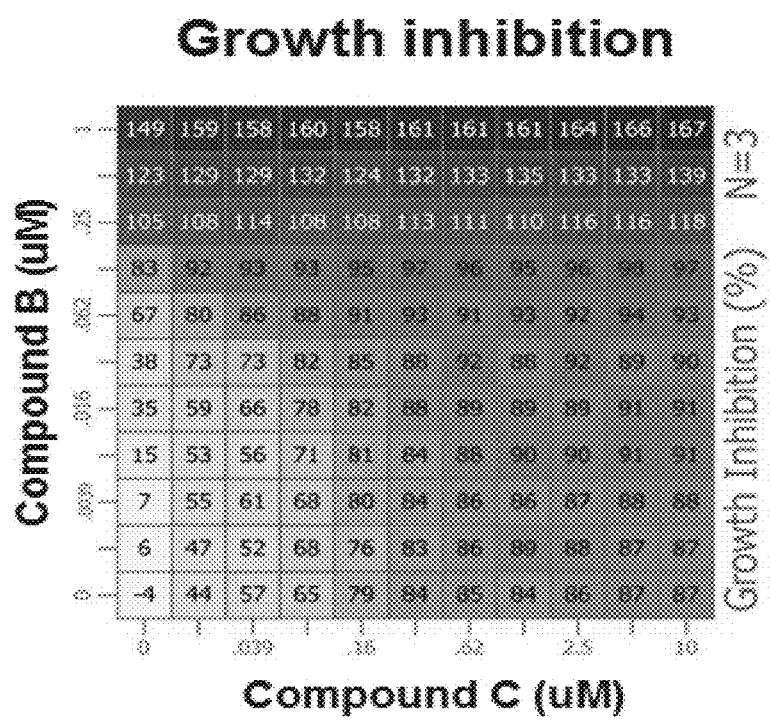

In combination (FIGS. 1 to 3), Compound B and Compound C treatment caused modest synergistic growth inhibition in LP6 cells. Synergy was calculated using the HSA model which measures the effect on growth relative to what would be expected from the most effective single agent dose. In LP6 cells, the Compound B/Compound C combination caused excess inhibition over most effective single agent doses. In 449b and 778 cell lines this synergy was not observed.

TABLE 2

IC50 Values and Synergy Scores.

| Cell Line | IC50 (nM) Compound B | IC50 (nM) Compound C | Synergy Score |
|---|---|---|---|
| 449b | 27.7 | 130 | 0.567 |
| 778 | 64.6 | 59.3 | 1.66 |
| LP6 | 86 | 475 | 1.32 |

Table 2 Legend: Displays additional data from the microscopy assay. The anti-proliferative activity of Compound B and Compound C was assessed via IC50 values (listed in nM). Potential synergistic interaction between Compound B and Compound C was assessed using a Synergy Score (Lehar et al., 2009) relative to the Loewe additivity model. Calculations were performed using Chalice software.

EXAMPLE 3: Different Dosing Regimens for the Combination of Compound B and Compound C Data in mice demonstrated that no or little efficacy was lost with intermittent dosing schedule in mice. It would be advised to distribute the same total dose per cycle in regards of safety, but may not necessary be the case. The intermittent dosing required higher dose that was administered intermittently compared to daily dose. The following dosing regimens can be thus used in the treatment:

| Regimen 1 | Regimen 2 (3 week-cycle) | Regimen 3 (4 week-cycle): |
|---|---|---|
| Compound B (QD, 2 w on, 2 w off) | Compound B (Q3W) | Compound B (Q4W) |
| Compound C (QD, 2 w on, 2 w off) | Compound C (QD, 2 w on/1 w off) | Compound C (QD, seq) |

The intermittend dosing of the compound B, namely every 3 weeks and every 4 weeks, leads to improved safety and less burden for patients.

EXAMPLE 4: Clinical Trial with the Combination of Compound B and Compound C

A clinical study can be performed to evaluate the combination of Compound B and Compound C in the clinic. In this study, the selection of the dose and dosing regimen of the two compounds can be based on the available human safety, efficacy and PK information for Compound C, and preclinical safety, efficacy and PK information for Compound B, as well as a predetermined assessment of the drug-drug interaction potential for this combination.

Study can be designed as a multi-center, open-label, study of Compound B in combination with Compound C, administered orally, in patients with liposarcoma who progressed on/or despite prior therapy. Both compounds can be dosed once daily for the first 2 weeks of a 4-week cycle (2 weeks on treatment, 2 weeks off treatment). Objectives and related endpoints as described in Table 3 can be determined.

TABLE 3

Objectives and related endpoints

| Objective | Endpoint |
|---|---|
| Primary | |
| *Phase Ib* | |
| To determine the MTD and/or RP2D of COMPOUND B in combination with COMPOUND C | Incidence of Dose Limiting Toxicities (DLTs) during the first cycle of treatment<br>Exposure to COMPOUND B and COMPOUND C as measured by PK parameters (AUC0-24 h at C1D14) |
| *Phase II* | |
| To assess the preliminary anti-tumor activity of COMPOUND B in combination with COMPOUND C in liposarcoma | PFS as per RECIST 1.1, assessed by investigator |
| Secondary | |
| *Phase Ib/II* | |
| To characterize the safety and tolerability of COMPOUND B in combination with COMPOUND C | Safety: Incidence and severity of AEs and SAEs, including changes in laboratory values, vital signs<br>Tolerability: Dose interruptions, reductions and dose intensity. |
| To characterize the pharmacokinetic (PK) properties of COMPOUND B in combination with COMPOUND C and potential metabolite/s when feasible | Time vs. plasma concentration profiles, PK parameters of COMPOUND B in combination with COMPOUND C and potential metabolite/s when feasible |
| To assess the pharmacodynamic (PD) effect of COMPOUND B in combination with COMPOUND C and a potential relationship with clinical outcome | Changes from baseline of PD markers:<br>In tumor tissue (e.g. p21, PUMA) |
| *Phase Ib* | |
| To assess preliminary anti-tumor activity of COMPOUND B in combination with COMPOUND C in liposarcoma | BOR, ORR and PFS as per RECIST v1.1, assessed by investigator |
| *Phase II* | |
| To further assess the anti-tumor activity of COMPOUND B in combination with COMPOUND C in liposarcoma | BOR, ORR and DOR as per Recist v 1.1 assessed by investigator<br>OS |
| Exploratory | |
| *Phase Ib/II* | |
| Model to describe PK/PD relationship | Dose concentration response (biomarkers and/or efficacy) relationship |
| To assess genetic alterations in multiple cancer related genes in tumor samples and to evaluate their relationship with clinical outcomes | Genetic alterations in multiple cancer related genes found in tumor samples at baseline and at disease progression. |

AE Adverse Event
BOR Best Overall Response
DLT Dose Limiting Toxicity
DOR Duration of Response
ORR Overall Response Rate
OS Overall Survival
p21 Cyclin-dependent kinase inhibitor 1
PD Pharmacodynamics
PFS Progression free survival
PK Pharmacokinetics
PUMA p53 upregulated modulator of apoptosis
RP2D Recommended Phase two Dose
SAE Serious Adverse Event

The invention claimed is:

1. A pharmaceutical combination comprising
   (i) (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, and
   (ii) 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof, for use in the treatment of liposarcoma.

2. The pharmaceutical combination according to claim 1 for simultaneous or sequential use of the (i) (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, and (ii) 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof, in the treatment of liposarcoma.

3. The pharmaceutical combination according to claim 1, further comprising at least one pharmaceutically acceptable carrier.

4. The pharmaceutical combination according to claim 1 in the form of a kit of parts for the combined administration, wherein the (i) (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof, and (ii) 7-Cyclopentyl-2-(5-piperazin-1-yl-pyridin-2-ylamino)-7H-pyrrolo[2,3-d]pyrimidine-6-carboxylic acid dimethylamide, or a pharmaceutically acceptable salt thereof, are administered jointly or independently at the same time or separately within time intervals, for use in the treatment of liposarcoma.

5. The pharmaceutical combination for use in the treatment of liposarcoma according to claim 1, wherein the liposarcoma is well differentiated liposarcoma (WDLPS) or dedifferentiated liposarcoma (DDLPS).

6. The pharmaceutical combination for use in the treatment of liposarcoma according to claim 1, wherein the cancer comprises co-amplified MDM2 and/or CDK4.

7. The pharmaceutical combination for use in the treatment of liposarcoma according to claim 1, wherein the liposarcoma comprises functional p53 or is p53 wild-type.

8. The pharmaceutical combination according to claim 1 in the form of a combination product or a pharmaceutical composition.

9. The pharmaceutical combination according to claim 1 for the manufacture of a medicament or a pharmaceutical product for the treatment of liposarcoma.

\* \* \* \* \*